(12) United States Patent
Hassan et al.

(10) Patent No.: US 7,652,174 B2
(45) Date of Patent: Jan. 26, 2010

(54) HIGH SHEAR PROCESS FOR THE PRODUCTION OF CHLORAL

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 0 days.

(21) Appl. No.: 12/137,455

(22) Filed: Jun. 11, 2008

(65) Prior Publication Data

US 2009/0005604 A1    Jan. 1, 2009

Related U.S. Application Data

(60) Provisional application No. 60/946,519, filed on Jun. 27, 2007.

(51) Int. Cl.
*C07C 45/63* (2006.01)
(52) U.S. Cl. .................................................. 568/458
(58) Field of Classification Search ................. 568/458
See application file for complete search history.

(56) References Cited

U.S. PATENT DOCUMENTS

| 3,996,300 | A | | 12/1976 | Ahlstrom |
| 4,513,152 | A | | 4/1985 | Schillawski |
| 4,628,122 | A | | 12/1986 | Kuntz et al. |
| 5,008,462 | A | * | 4/1991 | Ishizuka et al. ............. 568/466 |
| 6,866,411 | B1 | * | 3/2005 | Stelzer et al. ............... 366/136 |

FOREIGN PATENT DOCUMENTS

GB         644916 A        10/1950

* cited by examiner

*Primary Examiner*—Sikarl A Witherspoon
(74) *Attorney, Agent, or Firm*—Conley Rose, P.C.

(57) ABSTRACT

Use of a high shear mechanical device incorporated into a process for the production of chloral as a reactor device is capable of decreasing mass transfer limitations, thereby enhancing the chloral production process. A system for the production of chloral from acetaldehyde and chlorine, the system comprising a reactor and an external high shear device the outlet of which is fluidly connected to the inlet of the reactor; the high shear device capable of providing a dispersion of chlorine gas bubbles within a liquid, the bubbles having an average bubble diameter of less than about 100 μm.

13 Claims, 2 Drawing Sheets

HIGH SHEAR PROCESS FOR THE PRODUCTION OF CHLORAL

CROSS-REFERENCE TO RELATED APPLICATIONS

This application claims the benefit under 35 U.S.C. §119(e) of U.S. Provisional Patent Application No. 60/946,519 filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of chloral by chlorination of acetaldehyde, and more particularly to apparatus and methods for converting acetaldehyde to chloral, via liquid phase chlorination, in a high shear process. More specifically, the disclosure relates to the reduction of mass transfer limitations in apparatus and methods for converting acetaldehyde to chloral.

2. Background of the Invention

Chloral, $CCl_3CH=O$, also known as trichloroacetaldehyde or trichloroethanal is an organic halide discovered in 1832 by Justus von Liebig. Chloral in pure form is a colorless oily liquid soluble in alcohol and ether. Chloral reacts with water to form chloral hydrate which has medicinal properties as a potent sedative. Historically, chloral was reacted with chlorobenzene in the presence of sulfuric acid catalyst to form DDT in the pesticide industry.

Chloral is typically produced by the chlorination of ethanol or aldehyde. Specifically during the chlorination of aldehydes, the raw materials acetaldehyde or paraldehyde may be used. Due to loss of ethanol via formation of ethyl chloride and ethyl acid sulfate as well as environmental and waste disposal problems associated with production of these materials, the ethanol process has been largely replaced by aldehyde chlorination. Acetaldehyde chlorination is carried out via the reaction:

$$CH_3CHO + 3Cl_2 \rightarrow CCl_3CHO + 3HCl \quad (1)$$

Chloral is an unstable compound, making it highly reactive such that it may combine with many chemical substances, including itself, or decompose.

Conventionally, the commercial practice of manufacturing chloral from acetaldehyde involves adding water to the material undergoing chlorination to inhibit decomposition of dichloroacetaldehyde and chloral by their reactions with chlorine. Chloroform and carbon tetrachloride result from decomposition. Presumably the decomposition reactions are inhibited by formation of the hydrates.

The hydrates are much more stable and therefore production of crude chloral containing only trace amounts of dichloroacetaldehyde, without significant chloroform and carbon tetrachloride co-production, can be accomplished. The chlorination reaction in addition generates significant amounts of byproduct hydrogen chloride gas (HCl) some of which tends to be absorbed by the wet crude chloral. To produce the purified chloral from the wet crude product, water and HCl must be removed. Many patents discuss methods of wet crude chloral purification, including U.S. Pat. Nos. 4,513,152; 774,151; 2,443,183; 2,478,152; 2,478,741; 2,768,173; 955,589; and 661,092.

Accordingly, there is a need in the industry for improved methods of producing chloral from acetaldehyde and chlorine whereby production rates are increased, unwanted reactions are reduced, and milder reaction conditions, such as lower temperature and pressure, are commercially feasible.

SUMMARY OF THE INVENTION

A high shear system and process for accelerating chloral production is disclosed. The high shear process reduces mass transfer limitations, thereby enhancing the effective reaction rate and enabling a reduction in reactor temperature, a reduction in reactor pressure, a reduction in contact time, and/or an increase in product yield. In accordance with certain embodiments of the present disclosure, a process is provided that makes possible an increase in the rate of a liquid phase process for the production of chloral from acetaldehyde by providing for more optimal time, temperature, and pressure conditions than are conventionally used.

In an embodiment described in the present disclosure, a process employs a high shear mechanical reactor to provide enhanced time, temperature, and pressure reaction conditions resulting in accelerated chemical reactions between multiphase reactants. Further, a process disclosed in an embodiment described herein comprises the use of a pressurized high shear device to provide for the production of chloral without the need for high volume, high pressure reactors, or excess chlorine.

These and other embodiments, features, and advantages will be apparent in the following detailed description and drawings.

BRIEF DESCRIPTION OF THE DRAWINGS

For a more detailed description of a preferred embodiment described in the present disclosure, reference will now be made to the accompanying drawings, wherein.

DETAILED DESCRIPTION OF THE PREFERRED EMBODIMENTS

Overview

Figure 1:
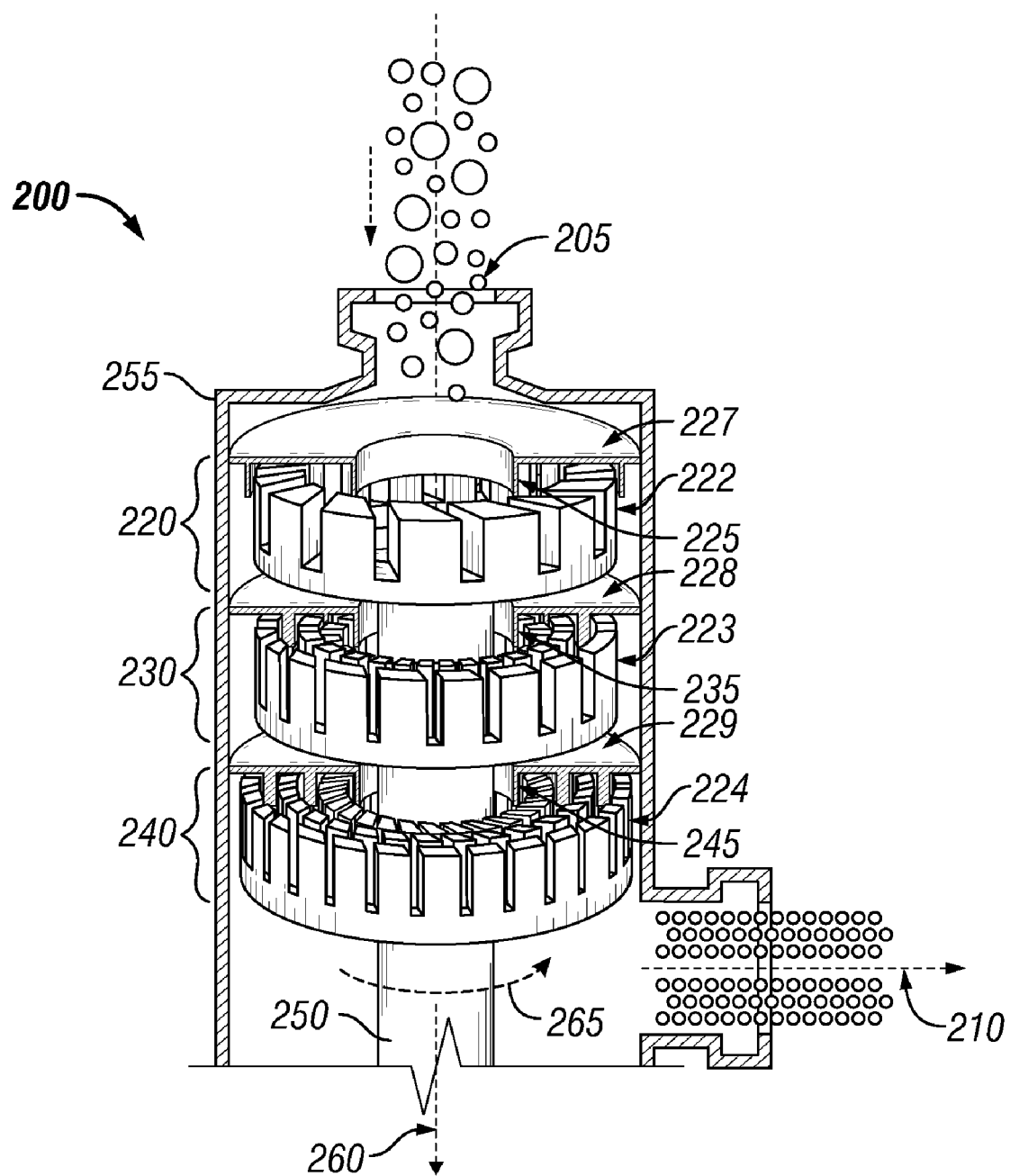
FIG. 1 is a cross-sectional diagram of a high shear device for the production of chloral.

An improved process and system for the production of chloral via chlorination of acetaldehyde employs an external or inline high shear mechanical device. The high shear device is a mechanical reactor, mixer, or mill to provide rapid contact and mixing of chemical ingredients in the device. Chloral production results from the chlorination of acetaldehyde or paraldehyde. These raw materials are collectively termed aldehydes hereinafter.

Chemical reactions involving liquids, gases, and solids rely on the laws of kinetics that involve time, temperature, and pressure to define the rate of reactions. In cases where it is desirable to react two or more raw materials of different phases (e.g. solid and liquid; liquid and gas; solid, liquid, and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants.

In conventional reactors, contact time for the reactants and/or catalyst is often controlled by mixing which provides contact with two or more reactants involved in a chemical reaction. A reactor assembly that comprises a high shear device makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes.

High Shear Device

High shear devices (HSD) such as a high shear mixer, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 μm Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 μm to about 1 μm. At the other end of the spectrum are high shear device systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy—high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 μm to about 25 μm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m³. In embodiments, the energy expenditure is in the range of from about 3000 W/m³ to about 7500 W/m³. The shear rate generated in a high shear device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec)=$\pi \cdot D \cdot n$, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, $2\pi R$, where R is the radius of the rotor (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external, mechanically-driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi), and elevated temperatures at the tip of the shear device are produced during operation. In certain embodiments, the local pressure is at least 1034 MPa. In further embodiments, the pressure is dependent on the viscosity of the solution, rotor tip speed, and shear gap.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid, or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm). The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam.

Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described above. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300-700 l/h (depending on generator), a tip speed of from 9.4-41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate the acetaldehyde into free radicals exposed to chlorine gas for the formation of chloral product.

Description of High Shear Chloral Production Process and System

Figure 2:
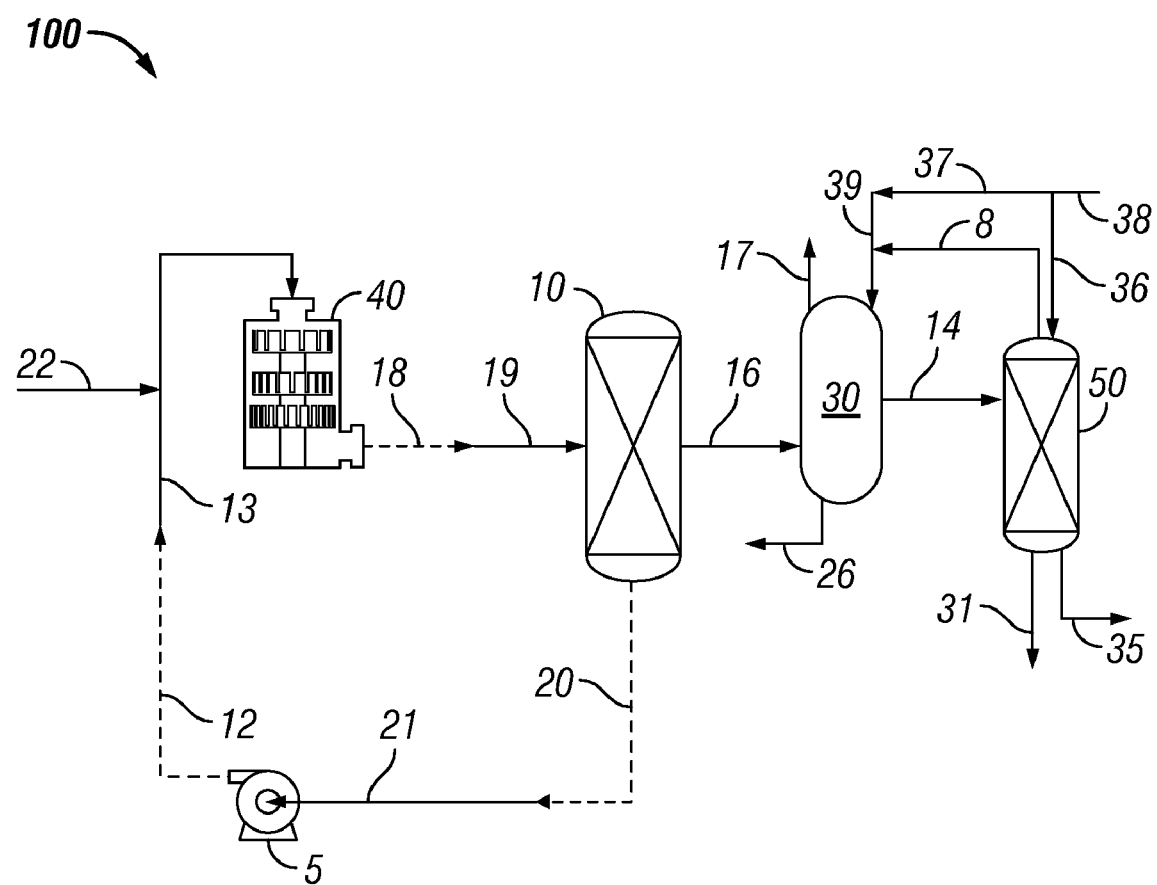
FIG. 2 is a process flow diagram according to an embodiment of the present disclosure for a mediator-assisted high shear process for production of chloral.

The high shear chloral production process and system of the present disclosure will now be described in relation to FIG. 2. FIG. 2 is a representative process flow diagram of a high shear system (HSS) 100 for the production of chloral from acetaldehyde and chlorine gas. FIG. 2 illustrates the basic components of a representative high shear chloral production system in which the process is carried out. These components comprise pump 5, high shear device (HSD) 40, and reactor 10. The high shear chloral production process and system create a chlorine (or other gaseous reactant) emulsion in the feed stream including aldehyde prior to introduction to the reactor 10.

Pump 5 is used to provide a controlled flow throughout high shear device 40 and HSS 100. In this way, HSS 100 uses high shear to enhance reactant intimate mixing. In embodiments, pump 5 increases the pressure of the reactant stream 21 to greater than about 203 kPa (2 atm). Alternatively, the pump 5 may pressurize reactant stream 21 to a pressure of greater than about 2030 kPa (20 atm). The increased pressure of reactant stream 21 can be used to accelerate reactions. The limiting factor for pressure in HSS 100 may be the pressure limitations of pump 5 and high shear device 40. Preferably, all contact parts of pump 5 comprise stainless steel. Pump 5 may be any suitable pump, for example, a Roper Type 1 gear pump, Roper Pump Company (Commerce Georgia) or a Dayton Pressure Booster Pump Model 2P372E, Dayton Electric Co. (Niles, Ill.).

Pump 5 pressurizes reactant stream 21. Reactant stream 21 comprises liquid aldehydes such as, but not limited to, acetaldehyde, paraldehyde (trimer of acetaldehyde), and similar compounds as are known to one of skill in the art. Reactant stream 21 may further comprise water. Likewise, acetaldehyde in different forms can be used. The prior art disclosed in U.S. Pat. Nos. 2,702,303 and 2,768,173 describes the use of acetaldehyde and its reversible polymers (e.g. paraldehyde, $(CH_3CHO)_3$), the former disclosing a completely aqueous process which is the usual commercial practice, and the latter disclosing a process of anhydrous chlorination of paraldehyde to the hexachloroparaldehyde state, followed by aqueous chlorination to crude chloral. The high shear system and process may be used for either method; the aqueous process with acetaldehyde as liquid solution will be described in detail.

The pump exit stream 12 comprises a pressurized stream analogous to the reactant stream 21. Pump exit stream 12 is in fluid communication with high shear device (HSD) inlet stream 13. In certain embodiments pump exit stream 12 and HSD inlet stream 13 are a continuous stream. Pump exit stream 12 may be mixed with dispersible gas stream 22 comprising chlorine gas. The dispersible gas stream 22 may be continuously fed into pump exit stream 12 to form HSD inlet stream 13. Dispersible gas stream 22 may be injected into HSD inlet stream 13.

Dispersible gas stream 22 and pressurized pump exit stream 12 are injected into HSD inlet stream 13 for processing by high shear device 40. HSD inlet stream 13 is in fluid communication with HSD 40. As discussed in detail above, high shear device 40 is a mechanical device that utilizes, for example, a stator rotor mixing head with a fixed gap between the stator and rotor. Dispersible gas stream 22 comprising chlorine is dispersed in pump exit stream 12 comprising aldehydes for the production of chloral. In high shear device 40, chlorine gas and liquid stream 12 are mixed to form an emulsion comprising microbubbles and nanobubbles of chlorine gas. In embodiments, the resultant dispersion comprises bubbles in the submicron size. In embodiments, the resultant dispersion has an average bubble size less than about 1.5 μm. In embodiments, the mean bubble size is less than from about 0.1 μm to about 1.5 μm. Not to be limited by a specific method, it is known in emulsion chemistry that submicron particles dispersed in a liquid undergo movement primarily through Brownian motion effects. Thus it is believed that submicron gas particles created by the high shear device 40 have greater mobility through boundary layers of solid catalyst particles thereby facilitating and accelerating the catalytic reaction through greater transport of reactants. In embodiments, the high shear mixing produces gas bubbles capable of remaining dispersed at atmospheric pressure for about 15 minutes or longer depending on the bubble size. In embodiments, the mean bubble size is less than about 400 nm; more preferably, less than about 100 nm. HSD 40 serves to create an emulsion of chlorine bubbles within high shear inlet stream 13 comprising aqueous aldehydes and chlorine gas. The emulsion may further comprise a micro-foam. In embodiments there may be several high shear devices 40 used in series.

The HSD exit stream 18 comprises the emulsion. HSD 18 is in fluid communication with reactor 10. In certain embodiments, HSD 18 undergoes further processing to form reactor inlet stream 19. Reactor inlet stream 19 enters reactor 10 for chloral production. Chlorination reactions will occur whenever suitable time, temperature, and pressure conditions exist. In this sense, chlorination could occur at any point in HSS 100 where temperature and pressure conditions are suitable. In such embodiments, a discrete reactor is often desirable to allow for increased residence time, agitation, and heating/cooling. Reactor 10 may be any reactor in which multiphase chlorination may propagate, as will be known by one skilled in the art. In embodiments, chloral production is continuous.

In embodiments, reactor 10 is a continuous stirred tank reactor. The reaction may be maintained at the specified reaction temperature, using cooling coils in the reactor 10 to maintain reaction temperature, as is known to those of skill in the art. The use of external heating and/or cooling heat exchange devices may regulate the reaction temperature. Suitable locations for external heat exchangers would be between the reactor 10 and the pump 5; between the pump 5 and the high shear mixer 40; and/or between the high shear device 40 and the reactor 10. There are many types of heat transfer devices that may be suitable and are known to those experienced in the art. Such exchangers include shell-and-tube, plate, and coil heat exchangers. Reactor 10 may further comprise a stirring system and level regulator as known to those of skill in the art. In certain embodiments, the reactor is maintained at a temperature of below about 40° C.

Reaction products are removed from the reactor by product stream 16. Product stream 16 may comprise chloral, water, dissolved HCl, and such commonly found contaminants as monochloroacetaldehyde, dichloroacetaldehyde, butyl chloral, the chloroacetic acids, carbon tetrachloride, and chloroform. Other contaminants may be present, depending on the conditions in the reactor, and the reactants for the chlorination that are utilized. Variations of ethanol or aldehyde processes for chloral production, known to one skilled in the art, will produce crude chloral amenable to purification Product stream 16 comprising chloral may be purified by any means known to those of skill in the art. For example, U.S. Pat. No. 4,513,152 describes introducing crude chloral to mixing vessel 30. Mixing vessel 30 is in fluid communication with sulfuric acid stream 37 obtained from a sulfuric acid source 38. Mixing vessel 30 is in fluid communication with sulfuric acid stream 37 by supply stream 39. In certain embodiments, supply stream 39 comprises processing the sulfuric acid. In certain embodiments, mixing vessel 30 comprises agitation and heating to remove hydrochloric acid. Hydrochloric acid byproduct may be removed by acid exit stream 17. In further embodiments, exit stream 17 may comprise a reflux condenser. Waste sulfuric acid stream 26 exits the process. Mixing vessel 30 produces a liquid chloral product stream 14.

Choral product stream 14 may be further treated in purifying reactor 50. Purifying reactor 50 comprises further treatment with sulfuric acid from sulfuric acid inlet 36, to further remove hydrochloric acid activity. The acids are removed from purifying reactor 50 by outlet 31, or by sulfuric acid recycle stream 8. Sulfuric acid stream 8 may be recycled to mixing vessel 30. The purified chloral exits purifying reactor 50 via chloral stream 35. In certain embodiments, chloral stream 35 further undergoes distillation. Chloral stream 35 may further undergo any process for refining chloral for additional chemical uses.

In embodiments there may be several high shear devices 40 used in series. Two or more high shear devices 40 such as high shear colloid devices are aligned in series, and are used to further enhance the reaction. Operation of multiple high shear devices 40 may be in either batch or continuous mode. In some instances in which a single pass or "once through" process is desired, the use of multiple high shear devices 40 in series may also be advantageous. Multiple high shear devices operated in series may permit the removal of reactor 10 from the high shear system 100. In some embodiments, multiple high shear devices 40 are operated in parallel, and the outlet dispersions therefrom are introduced into one or more reactor(s) 10.

The application of enhanced mixing of the reactants by high shear device 40 results in greater conversion of acetaldehyde to chloral in some embodiments of the process. Further, the enhanced mixing of the chlorine in the aqueous aldehyde solution provides an increase in throughput of the process stream of the high shear system 100. In certain instances, the high shear device 40 is incorporated into an established process, thereby enabling an increase in production (i.e., greater throughput). In contrast to some existing methods that attempt to increase the degree of conversion of aldehyde by increasing reactor pressures, the superior dissolution and/or emulsification provided by high shear mixing allows in many cases a decrease in overall operating pressure while maintaining or even increasing reaction rate.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural or other details supplementary to those set forth herein.

We claim:

1. A method for producing choral, the method comprising:
   forming a mixture by combining a dispersable gas stream comprising chlorine and a reactant stream comprising liquid aldehyde;
   forming a dispersion from the mixture comprising liquid aldehyde and chlorine gas by introducing the mixture into a high shear device, wherein the dispersion comprises chlorine gas bubbles with a mean diameter of less than about 5 μm, and wherein the high shear device comprises at least one rotor and at least one stator; and
   introducing the dispersion into a reactor from which a product comprising chloral is removed, wherein the operating temperature within the reactor is maintained at a temperature of less than about 40° C.

2. The method of claim 1 further comprising pumping an aqueous stream comprising the liquid aldehyde to a pressure of at least about 203 kPa to produce a pressurized aqueous stream.

3. The method of claim 1 wherein the chlorine gas bubbles in the dispersion have an average diameter of less than about 1.5 μm.

4. The method of claim 1 wherein forming the dispersion comprises rotating the at least one rotor at a tip speed of at least 5 m/s.

5. The method of claim 1 wherein forming the dispersion comprises rotating the at least one rotor at a tip speed of at least about 20 m/s.

6. The method of claim 4 wherein forming the dispersion comprises producing a localized pressure of about 1000 MPa at the tip of the at least one rotor.

7. The method of claim 1 wherein forming the dispersion comprises subjecting the chlorine gas and liquid aldehyde to a shear rate of greater than about 20,000 $s^{-1}$.

8. The method of claim 1 wherein forming the dispersion comprises an energy expenditure of at least 1000 $W/m^3$.

9. The method of claim 1 wherein the dispersion comprises a micro-foam.

10. The method of claim 1 further comprising treating the product with sulfuric acid.

11. The method of claim 1 wherein the liquid aldehyde comprises acetaldehyde, paraldehyde, or a combination thereof.

12. A method for producing chloral, the method comprising:
    providing a mixture of chlorine gas in aqueous solution comprising aldehyde; and
    forming a dispersion of chlorine gas bubbles in the aqueous solution comprising aldehyde by introducing the mixture into a high shear device and subjecting the mixture of liquid aldehyde and chlorine gas to a shear rate of at least 20,000 $s^{-1}$.

13. The method of claim 12 wherein the high shear device comprises at least one rotor and at least one stator.

* * * * *